US008765119B2

(12) United States Patent
Garbuzova-Davis et al.

(10) Patent No.: US 8,765,119 B2
(45) Date of Patent: Jul. 1, 2014

(54) TREATING AMYOTROPHIC LATERAL SCLEROSIS (ALS) WITH ISOLATED ALDEHYDE DEHYDROGENASE-POSITIVE UMBILICAL CORD BLOOD CELLS

(75) Inventors: Svitlana Garbuzova-Davis, Tampa, FL (US); Andrew Balber, Durham, NC (US); Cyndy Davis-Sanberg, Spring Hill, FL (US); Tracy Gentry, Durham, NC (US); Nicole Kuzmin-Nichols, Brandon, FL (US); Paul R Sanberg, Spring Hill, FL (US); Alison Willing, Tampa, FL (US)

(73) Assignees: University of South Florida, Tampa, FL (US); Saneron CCEL Therapeutics, Inc., Tampa, FL (US); StemCo Biomedical, Inc., Durham, NC (US)

( * ) Notice: Subject to any disclaimer, the term of this patent is extended or adjusted under 35 U.S.C. 154(b) by 522 days.

(21) Appl. No.: 10/908,322

(22) Filed: May 6, 2005

(65) Prior Publication Data

US 2005/0249708 A1    Nov. 10, 2005

Related U.S. Application Data

(60) Provisional application No. 60/521,493, filed on May 6, 2004.

(51) Int. Cl.
| A01N 63/00 | (2006.01) |
| A61K 35/28 | (2006.01) |
| A61K 35/48 | (2006.01) |
| A61K 35/12 | (2006.01) |
| A61K 35/50 | (2006.01) |
| A61K 35/30 | (2006.01) |
| A61K 9/00  | (2006.01) |
| C12N 5/0789 | (2010.01) |
| C12N 5/071  | (2010.01) |
| C12N 5/074  | (2010.01) |
| C12N 5/0775 | (2010.01) |

(52) U.S. Cl.
CPC .......... *A61K 35/28* (2013.01); *A61K 35/51* (2013.01); *A61K 2035/124* (2013.01); *A61K 35/50* (2013.01); *A61K 35/30* (2013.01); *A61K 9/0085* (2013.01); *C12N 5/0647* (2013.01); *C12N 5/0663* (2013.01); *C12N 5/0607* (2013.01); *C12N 5/0675* (2013.01); *C12N 2506/11* (2013.01)
USPC ........................................ 424/93.7; 424/93.1

(58) Field of Classification Search
CPC . A61K 35/28; A61K 35/51; A61K 2035/124; A61K 35/50; A61K 35/30; A61K 9/0085; C12N 9/0647; C12N 5/0663; C12N 5/0607; C12N 5/0675; C12N 2506/11
USPC ............................. 424/93.7; 435/377
See application file for complete search history.

(56) References Cited

U.S. PATENT DOCUMENTS

| 6,528,245 B2 * | 3/2003 | Sanchez-Ramos et al. ... 435/1.1 |
| 2002/0028510 A1 * | 3/2002 | Sanberg et al. ............... 435/368 |
| 2002/0132343 A1 * | 9/2002 | Lum ............................ 435/372 |
| 2004/0023318 A1 * | 2/2004 | Smith et al. .................... 435/25 |

FOREIGN PATENT DOCUMENTS

| WO | WO 96/31233 | * 10/1996 | ............. A61K 38/48 |
| WO | WO 2005/001078 A2 | * 1/2005 | |

OTHER PUBLICATIONS

Shieh et al. State-of-the-art tissue engineering: From tissue engineering to organ building. Surgery (Jan. 2005) vol. 137(1), pp. 1-7.*
Dawson et al. Safety issues in cell-based intervention trials. Fertility and Sterility (2003) vol. 80(5), pp. 1077-1085.*
LeRou et al. Therapeutic potential of embryonic stem cells. Blood Reviews (2005), pp. 1-11.*
Nagy et al. Stem cell transplantation as therapeutic approach to organ failure. Journal of Surgical Research (available online Sep. 27, 2005), pp. 1-9.*
Gunning, J. Umbilical cord cell banking—implications for the future. Toxicology and Applied Pharmacology, (2005), vol. 207, pp. S538-S543.*
Silani et al. Stem cell therapy for amyotrophic lateral sclerosis. Lancet (2004), vol. 364, pp. 200-202.*
Tai et al. Stem cells as a potential treatment of neurological disorders. Curent Opinion in Pharmacology (2004), vol. 4, pp. 98-104.*
Chen et al. The potential for the use of mononuclear cells from human umbilical cord blood in the treatmetn of amyotrophic lateral sclerosis in SOD1 mice. Journal of Medicine (2000) vol. 31, Nos. 1 and 2, pp. 21-30.*
Garbuzova-Davis et al. Intravenous and intraspinal transplantation of umbilical cord blood cells in a mouse model of familial amyotrophic lateral sclerosis. Program No. 852.13.2002 Abstract Viewer/Itinerary Planner. Washington, DC: Society for Neuroscience, 2002. Online. (abstract).*
Janson et al. Human intrathecal transplantation of peripheral blood stem cells in amyotrophic lateral sclerosis. Journal of Hematotherapy and Stem Cell Research (2001), vol. 10, pp. 913-915.*
Barker et al. Umbilical cord blood tranplantation: current preactice and future innovations. Critical Reviews in Oncology and Hematology (2003) vol. 48, pp. 35-43.*
Storb et al., 1999, Blood, 94: 1131-1136.*
Sanchez-Ramos et al., 2001, Experimental Neurology, 171: 109-115.*
Storms et al., 1999, PNAS, USA, 96: 9118-9123.*
Ho et al., 2001, Blood, 98: 3192-3204.*
Hao et al., Journal of Hematotherapy and Stem Cell Research 12: 23-32, 2003 dc Feb. 11, 2014.

(Continued)

*Primary Examiner* — Deborah Crouch
(74) *Attorney, Agent, or Firm* — Robert J. Varkonyi; Smith & Hopen, P.A.

(57) ABSTRACT

A method of treating a patient with a neurodegenerative disease, such as ALS, using progenitor cells isolated from human umbilical cord blood. Non-invasive transplantation of aldehyde dehydrogenase (ALDH$^+$) expressing progenitor cells provides cell replacement and protection of motor neurons.

10 Claims, 8 Drawing Sheets

(56) References Cited

OTHER PUBLICATIONS

Cai et al., 2003, Blood Cells, Molecules, and Disease, 31, 18-27.
Blaha et al., 2003, Blood, 101: 2886-2893.
Saleh, et al. 2009. "Evaluation of Humoral Immune Response in Adaptive Immunity in ALS Patients During Disease Progression." Journal of Neuroimmunology. vol. 215. pp. 96-101.
Kuzmenok, et al. 2006. "Lymphopenia and Spontaneous Autorosette Formation in SOD1 Mouse Model of ALS." Journal of Neuroimmunology. vol. 172. pp. 132-136.
Garbuzova-Davis, et al. 2004. "Progenitor/Stem Cells Derived from Umbilical Cord Blood Delay Disease Symptoms and Increase Lifespan in ALS Mice." Presentation No. 312.15. Neuroscience Meeting Planner. San Diego, CA: Society for Neuroscience. Online.
Garbuzova-Davis, et al. 2004. "Human Umbilical Cord Blood Cells as a Potential Cell Source for Treatment of ALS." Eleventh Annual Conference of the ASNTR-Abstracts/Experimental Neurology. vol. 187. pp. 208-209.
Gupta, et al.; "Possible Association Between Expression of Chemokine Receptor-2 (CCRs) and Amyotrophic Lateral Sclerosis (ALS) Patients of North India"; PLoS ONE; vol. 7, Issue 6, pp. 1-8, 2012.
Lewis, et al.; "The Neuroinflammatory Response in ALS: The Roles of Microglia and T Cells"; Neurology Research International; vol. 2012, pp. 1-8; 2012.
ncbi.nlm.nih.gov; "Amyotrophic Lateral Sclerosis"; U.S. National Library of Medicine—The World's Largest Medical Library; http://.ncbi.nlm.nih.gov/pubmedhealth/PMH00017081; Accessed on Jun. 13, 2012.
Jennifer D. Newcomb, Timing of Cord Blood Treatment After Experimental Stroke Determines Therapeutic Efficacy, Cell Transplantation; vol. 15, pp. 213-223, 2006.
Svitlana Garbuzova-Davis, Transplantation of Human Umbilical Cord Blood Cells Benefits an Animal Model of Sanfilippo Syndrome Type B, Stem Cells and Development 14: 384-394 (2005).
Stefania Corti, Transplanted ALDHhi SSClo Neural Stem Cells Generate Motor Neurons and Delay Disease Progression of nmd Mice, an Animal Model of SMARD1, Human Molecular Genetics, 2006, vol. 15, No. 2.
Martina Vendrame, Infusion of Human Umbilical Cord Blood Cells in a Rat Model of Stroke Dose-Dependently Rescues Behavioral Deficits and Reduces Infarct Volume, www.strokeaha.org, 2004 dc Feb. 11, 2014.
Martina Vendrame, Cord Blood Rescues Stroke-Induced Changes in Splenocyte Phenotype and Function, Experimental Neurology 199, 2006, 191-200.

\* cited by examiner

CD34 Expression in Various Lymphoid Organs in Treated and
Untreated G93A Mice (Summary)

| Groups | Organs | | | | | | | |
|---|---|---|---|---|---|---|---|---|
| | Bone Marrow | | Spleen | | Lymph nodes | | Peripheral Blood | |
| | host | donor | host | donor | host | donor | host | donor |
| ALDH | - | + | + | + | + | + | - | + |
| Hucb | - | + | + | + | + | + | - | + |
| No-Tx | + | | + | | + | | - | |

Fig. 2

TREATING AMYOTROPHIC LATERAL SCLEROSIS (ALS) WITH ISOLATED ALDEHYDE DEHYDROGENASE-POSITIVE UMBILICAL CORD BLOOD CELLS

CROSS REFERENCE TO RELATED APPLICATIONS

This application claims priority to U.S. Provisional Patent Application No. 60/521,493, having the same title and inventorship.

BACKGROUND OF THE INVENTION

Amyotrophic lateral sclerosis (ALS) is a fatal degenerative disease affecting motor neurons in the spinal cord, brainstem, and cortex. This disease clinically manifests as progressive muscular weakness and atrophy, leading to paralysis and death within 3-5 years of diagnosis. Treatments are only palliative. Neural transplantation may be able to restore lost neuromotor function and/or prevent motoneural degeneration. Because of the widespread degeneration of motor neurons in ALS, neural transplantation is not often considered a therapeutic option.

However, we recently demonstrated that the onset of motor dysfunction can be delayed and lifespan possibly extended when hNT Neurons are transplanted into the spinal cord of the transgenic mouse (SOD1, G93A) model of this disease. Since the hNT Neurons are postmitotic, terminally differentiated human neuronal-like cells, they must be transplanted directly into the injury site, not a practical treatment approach in ALS.

A better approach may be to administer a cell that migrates through the neural axis to the specific regions of neurodegeneration, such as neural stem cells. Most tissue used in neural transplantation protocols is now obtained from a human fetus, including the majority of stem cells. Ethical issues with the use of this fetal tissue make it necessary to locate alternative cell sources with the putative ability to migrate in the host to the site of injury or disease and differentiate into the required cell type. Stem cells from human umbilical cord blood (hUCB) may be preferable to other sources because they are obtained after delivery, so there is no risk to mother or child, and are more easily available than either bone marrow or neural stem cells.

The mononuclear cell fraction from human UCB is relatively rich in multipotent progenitors with extensive proliferation capacity. However, hematopoietic stem cells are only present at low levels (2% of mononuclear cells). Isolation and purification techniques of hematopoietic stem cells and other progenitors from human bone marrow and UCB have been developed, based on the expression of cell surface markers (CD34, CD38 Sca-1, thy-1, etc.) or on size and cell density, or other metrics. These techniques, however, are complex, too costly, and inefficient to be well suited to a clinical environment. In addition, cell populations resulting from these techniques are often heterogeneous with degraded functional activity and overlap between hematopoietic stem cells and mature progenitors.

The enzyme aldehyde dehydrogenase (ALDH) is found at relatively high levels in hematopoietic progenitors. Storms et al. (1999) suggest that "because high-level expression of ALDH appears to be an intrinsic property of a variety of stem cells, isolating primitive hematopoietic cells on the basis of ALDH activity may not be affected as significantly by the stem cell source, genetic background, or stem cell manipulation as other stem cell isolation methods." This high level of ALDH activity may not be surprising given that retinoic acid (RA) is so critical in embryological development. Multiple isoforms of this enzyme are critical in the conversion of retinal or retinaldehyde to RA. The observation that these cells respond to RA+NGF (nerve growth factor) by differentiating into cells that express neural markers suggest that there may be an autocrine mechanism in this progenitor population that could be exploited.

SUMMARY OF INVENTION

In vitro studies have shown that the UCB cells exposed to RA and NGF can differentiate into neural phenotypes and express molecular neuronal/glial markers. Moreover, transplanted UCB cells in a rodent stroke model can migrate to regions of degeneration and ameliorate behavioral deficits. These results indicate that UCB has therapeutic potential for repair of an injured nervous system and produce behavioral recovery. In studies by Ende and associates, intravenous administration of large doses ($35 \times 10^6$) UCB cells into irradiated SOD1 mice has been shown to increase lifespan by almost 40%. While the survival data is impressive, the researchers did not examine motor function in these animals or determine the mechanism underlying this effect. Significantly, stem cells were only a small proportion of the UCB population in these studies. Using the proposed isolation techniques on UCB yields surprising and unexpected results of superior enrichment of stem cells and enhanced transplant effects.

In one embodiment, the present invention includes a method of treating a subject with a neurodegenerative disorder, such as ALS, comprising the steps of isolating at least one progenitor cell from human umbilical cord blood and administering to the subject a therapeutically effective amount of the progenitor cell. The progenitor cell is chosen from the group consisting of hematopoietic progenitor cells, human umbilical cord blood cells and combinations thereof (rather than cells chosen from the mononuclear compartment).

In a preferred embodiment the hematopoietic progenitor cells express aldehyde dehydrogenase. A distinct advantage of the present invention is that the therapeutically effective amount of the progenitor cell can be administered intravenously. An immunosuppressant can be administered to the subject following treatment to reduce the risk of rejection of the transfused cells; yet impressive results were achieved without the use of immunosuppressants.

In another embodiment the isolated progenitor cell is exposed to retinoic acid and neural growth factor. The culturing in retinoic acid and neural growth factor to induce the progenitor cells to differentiate into neural phenotypes and express molecular neuronal/glial markers.

In yet another embodiment, the present invention provides a method of treating a subject with a neural injury, comprising the steps of isolating at least one progenitor cell from human umbilical cord blood and administering to the subject a therapeutically effective amount of the progenitor cell. The progenitor cell is chosen from the group consisting of hematopoietic progenitor cells, human umbilical cord blood cells and combinations thereof (rather than cells chosen from the mononuclear compartment).

BRIEF DESCRIPTION OF THE DRAWINGS

For a fuller understanding of the nature and objects of the invention, reference should be made to the following detailed description, taken in connection with the accompanying drawings, in which:

FIG. 2 is a table showing CD34 expression various lymphoid organs in treated and untreated G93A mice.

DETAILED DESCRIPTION OF THE PREFERRED EMBODIMENT

Figure 1:
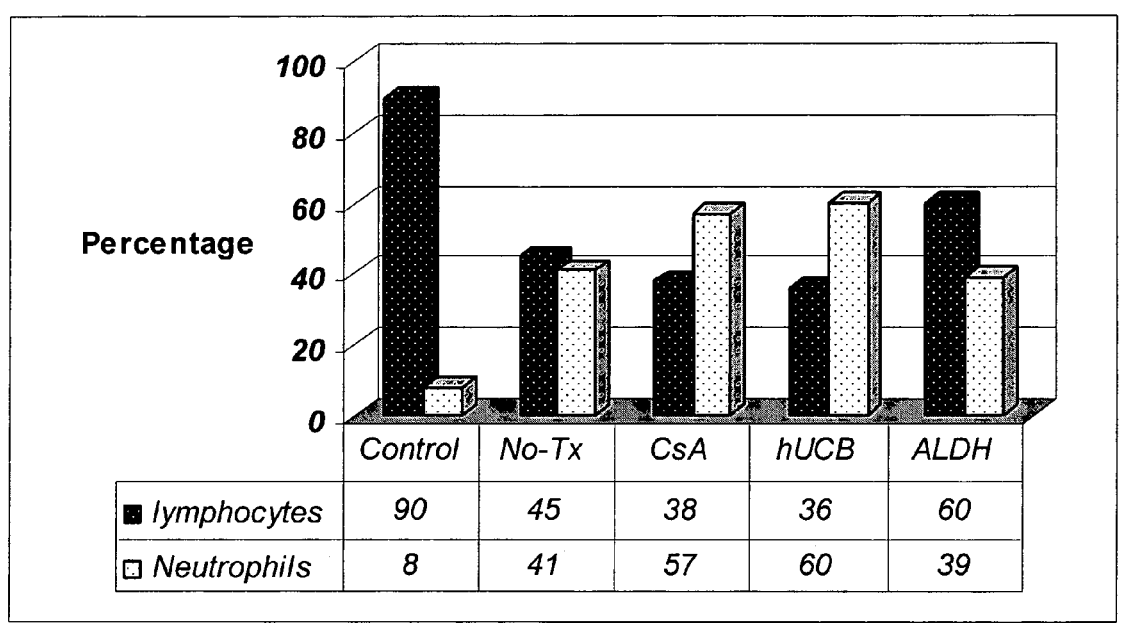
FIG. 1 is a graph comparing the percentage of lymphocytes and neutrophils present in the peripheral blood from various treated, untreated and control animals.
Figure 3:
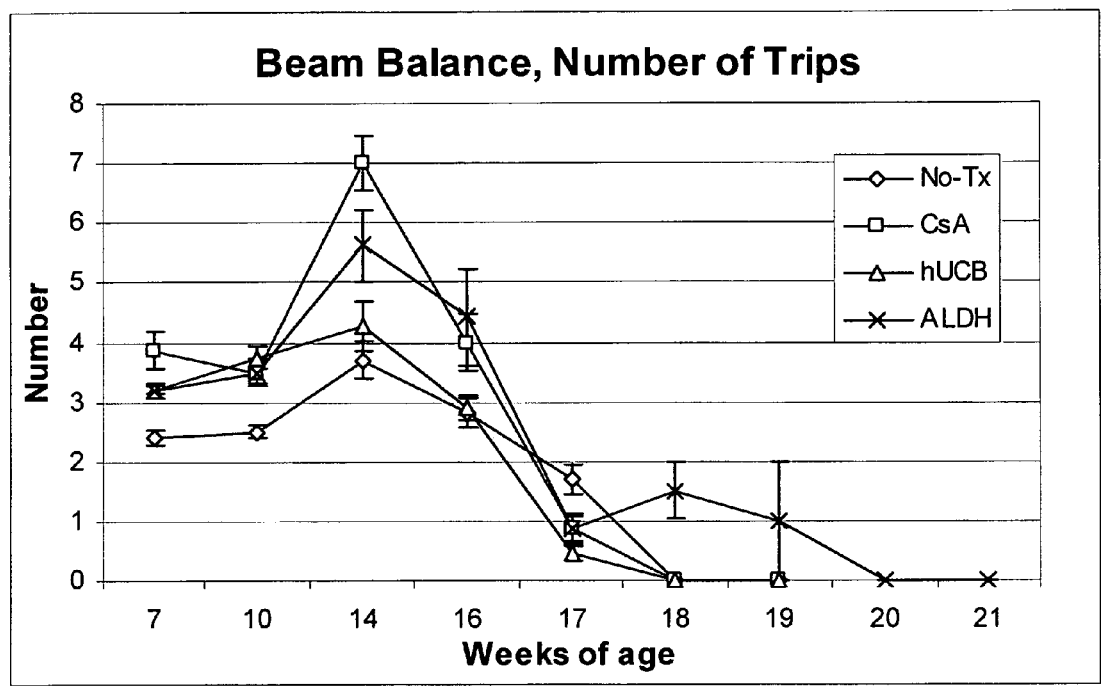
FIG. 3 is a graph showing behavioral data for beam balance, indicating the number of trips.
Figure 4:
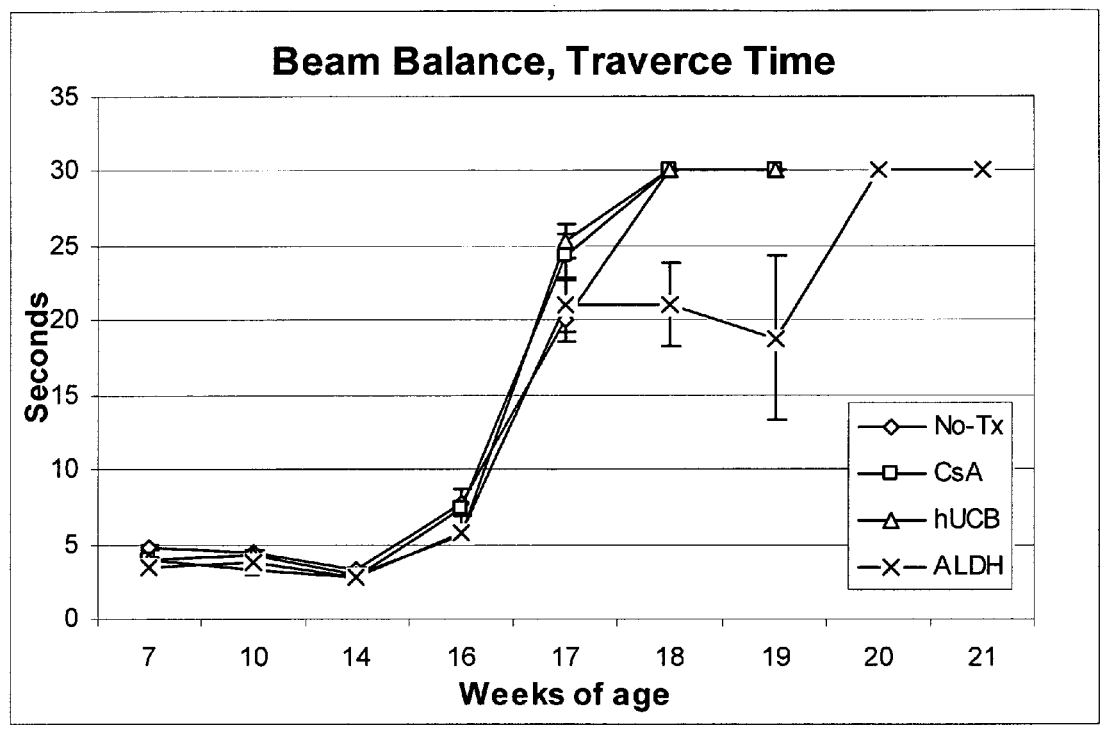
FIG. 4 is a graph showing behavioral data for beam balance, indicating the traverse time.
Figure 5:
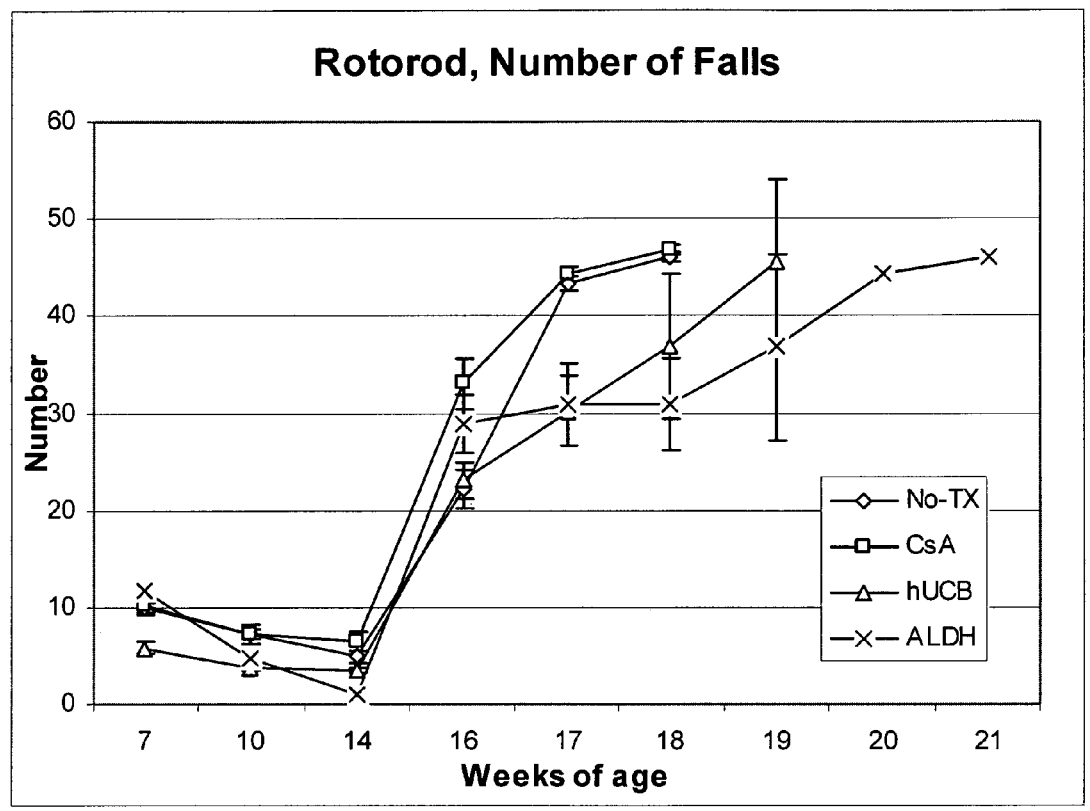
FIG. 5 is a graph showing behavioral data for the rotorod, indicating the number of falls.
Figure 6:
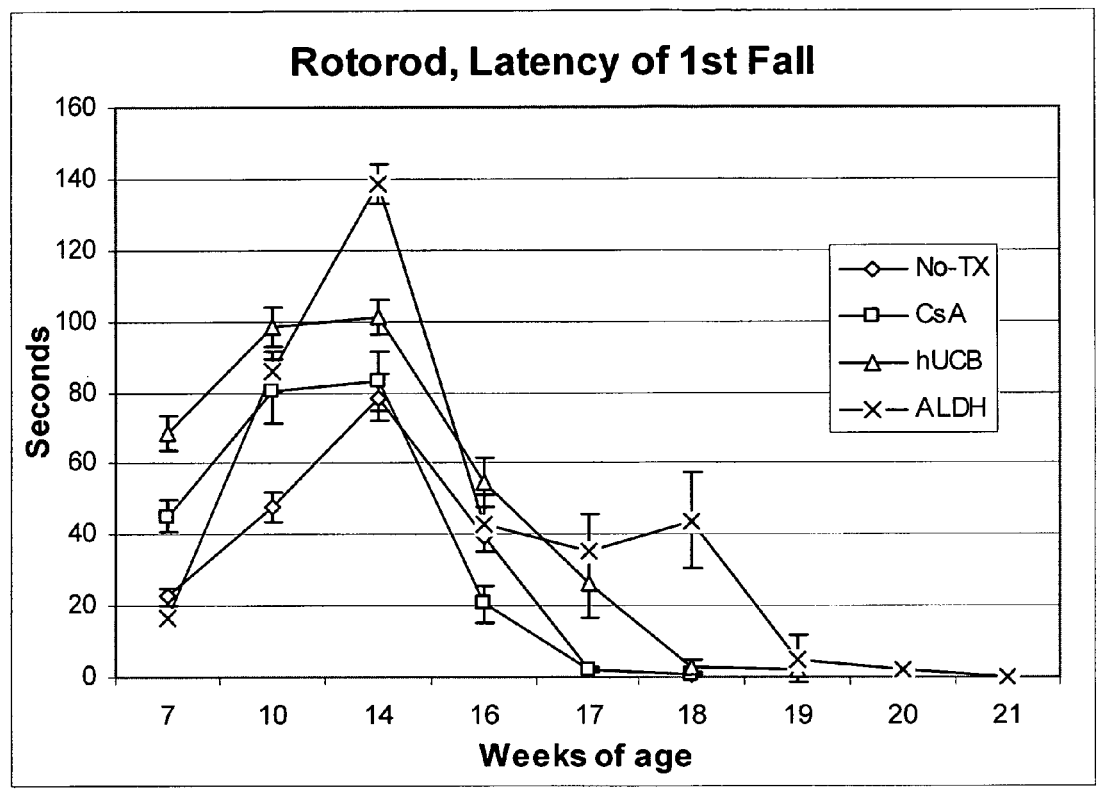
FIG. 6 is a graph showing behavioral data for the rotorod, indicating the latency of the first fall.
Figure 7:
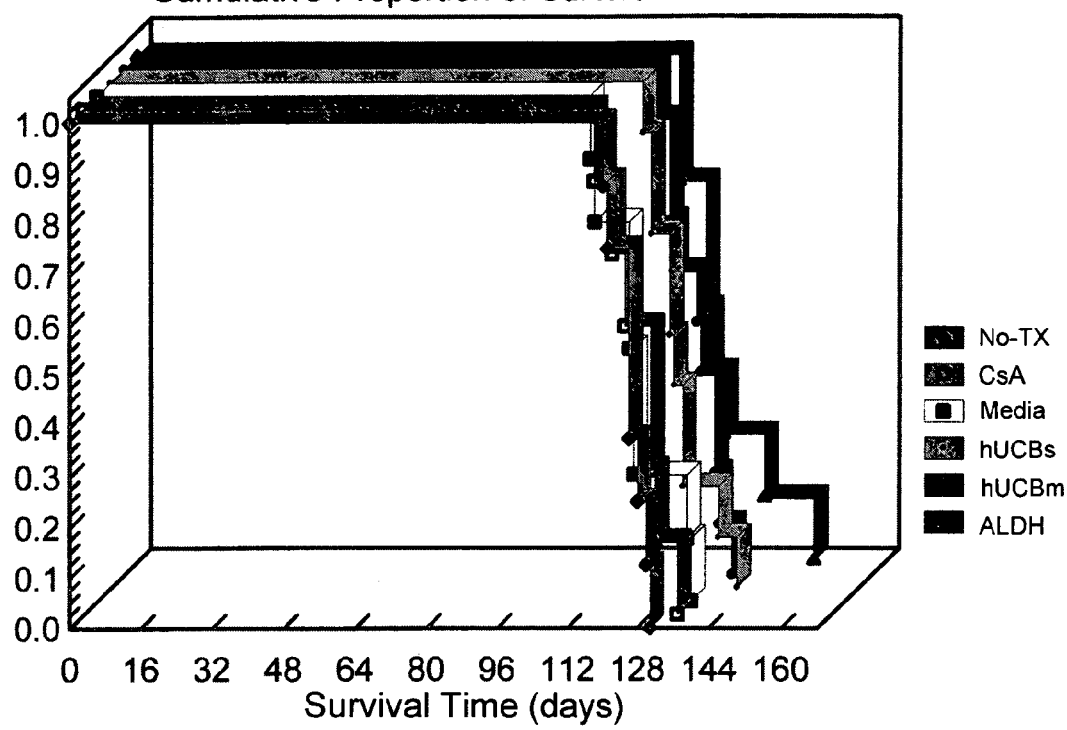
FIG. 7 shows a Kaplan-Meier cumulative survival plot for subjects.
Figure 8:
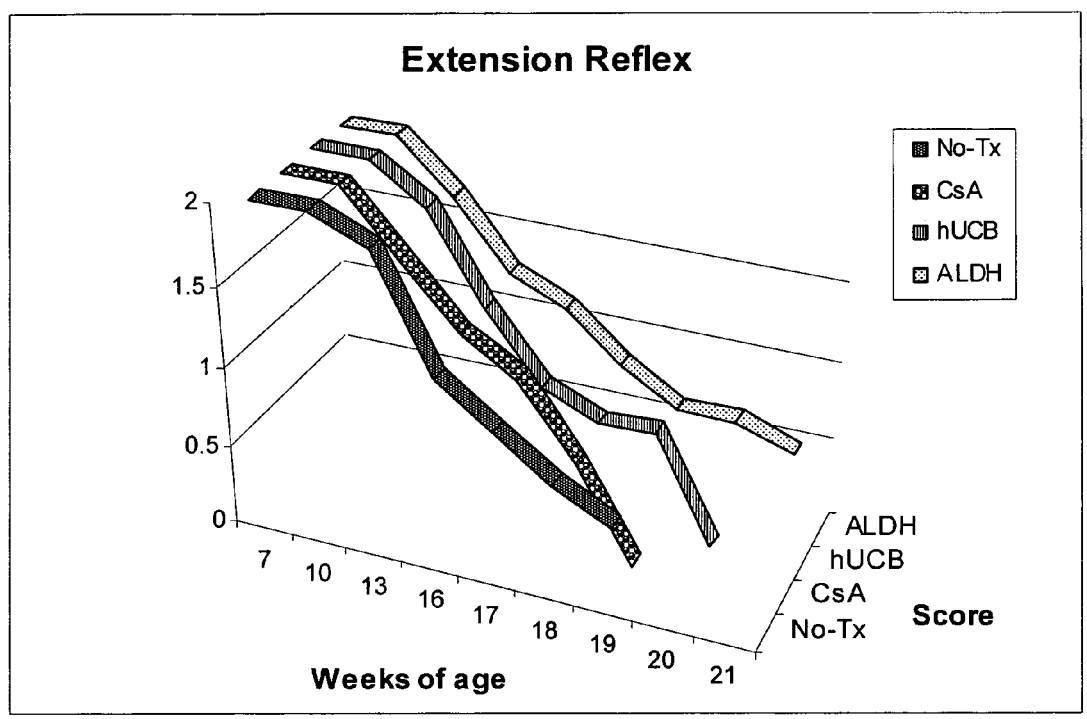
FIG. 8 is a graph showing behavioral data indicating extension reflex.

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

The pharmaceutical compositions of the subject invention can be formulated according to known methods for preparing pharmaceutically useful compositions. Furthermore, as used herein, the phrase "pharmaceutically acceptable carrier" means any of the standard pharmaceutically acceptable carriers. The pharmaceutically acceptable carrier can include diluents, adjuvants, and vehicles, as well as implant carriers, and inert, non-toxic solid or liquid fillers, diluents, or encapsulating material that does not react with the active ingredients of the invention. Examples include, but are not limited to, phosphate buffered saline, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils. Formulations are described in a number of sources that are well known and readily available to those skilled in the art. For example, *Remington's Pharmaceutical Sciences* (Martin E W [1995] Easton Pa., Mack Publishing Company, 19th ed.) describes formulations which can be used in connection with the subject invention.

Formulations suitable for parenteral administration include, for example, aqueous sterile injection solutions, which may contain antioxidants, buffers, bacteriostats, and solutes which render the formulation isotonic with the blood of the intended recipient; and aqueous and nonaqueous sterile suspensions which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the formulations of the subject invention can include other agents conventional in the art having regard to the type of formulation in question. The pharmaceutical composition can be adapted for various forms of administration. Administration can be continuous or at distinct intervals as can be determined by a person skilled in the art.

The administration of umbilical cord cells, ALDH+ cells, or any combination thereof is administered and dosed in accordance with good medical practice, taking into account the clinical condition of the individual patient, the site and method of administration, scheduling of administration, patient age, sex, body weight, and other factors known to medical practitioners.

The "therapeutically effective amount" for purposes herein is thus determined by such considerations as are known in the art. A therapeutically effective amount of the umbilical cord cells, ALDH+ cells, or any combination thereof is that amount necessary to provide a therapeutically effective result in vivo. The amount of umbilical cord cells, ALDH+ cells, or any combination thereof must be effective to achieve a response, including but not limited to total prevention of (e.g., protection against) and to improved survival rate or more rapid recovery, or improvement or elimination of symptoms associated with neurodegenerative disorders (such as ALS), neural damage, or other indicators as are selected as appropriate measures by those skilled in the art. In accordance with the present invention, a suitable single dose size is a dose that is capable of preventing or alleviating (reducing or eliminating) a symptom in a patient when administered one or more times over a suitable time period. One of skill in the art can readily determine appropriate single dose sizes for systemic administration based on the size of a mammal and the route of administration.

Example 1

Preparation of the hUCB and ALDH Cells and Transplantation Procedure.

Cryopreserved hUCB cells (Saneron CCEL Therapeutics Inc., Tampa, Fla.) and ALDH+ cells (STEMCO Biomedical Inc, NC) were thawed rapidly into Isolyte S, pH 7.4 (BBraun/McGaw Pharmaceuticals) and centrifuged (1000 rpm/7 min). The supernatant was discarded and the process repeated. After the final wash, viability and cell numbers were assessed using the 0.4% trypan blue dye exclusion method prior to and following transplantation. The cell concentration was adjusted to 300,000 cells/$\mu$l for hUCB cells ($3\times10^6$) or 3,000 cells/$\mu$l for ALDH$^+$ cells ($9\times10^3$) (Isolyte S, pH 7.4) were delivered unilaterally into the lateral ventricle of mice using the stereotaxic coordinates (AP+0.38 mm; ML+/−0.8 mm; DV=2.0 mm). The injection was delivered at the rate of 0.5 $\mu$l/minute. The needle was left in place for an additional 5 minutes after the injection and then withdrawn slowly. The incision was closed with VETBOND. These animals were immunosuppressed with cyclosporin (10 mg/kg ip per day) during the post-transplantation period.

Differential white blood cell count and Blood and Bone Marrow Smears.

At the end-stage of the disease during perfusion, blood was taken by heart puncture and a complete blood analysis and differential white blood cell count was performed (Antech Diagnostics). Blood smears were made from the snips of the animal tails, and bone marrow smears were made by extracting bone marrow from the tibia and femur bones. The smears were then fixed with Methanol for 4-6 minutes.

Immunohistochemistry identifying hematopoietic antigen expression on hUCB cells.

In vivo: Blood and bone marrow smears along with spleen and lymph node tissue of previously transplanted mice (n=30) were used. The organs were removed, post-fixed, and then cryoprotected in 20% sucrose in 0.1 M phosphate buffer (pH 7.2) overnight. Thirty μm coronal or sagittal sections were cut on a cryostat. Serial sections of the spleens and lymph nodes were thaw-mounted on slides, washed with deionized water to remove the freezing medium, and then rinsed several times in PBS. The tissue was then placed in 1% normal human serum (NhuS) in PBS, 0.5% TritonX100 for 30 minutes at room temperature. The sections were then placed in an antibody cocktail of mouse monoclonal antibody directed against human mitochondria (HuMit, 1:50, Chemicon) and monovalent goat anti-mouse Fab' fragment conjugated to FITC (1:200) which had previously been incubated for two hours at room temperature. After incubating the tissue overnight at 4° C., sections were rinsed in PBS. The spleen and lymph node tissue were then double-stained with the mouse monoclonal antibody for CD34 (1:50, Santa Cruz Biotechnology, Inc.). The next day after several washes in PBS, the slides were incubated with goat anti-mouse secondary antibodies conjugated to rhodamine (1:700, Molecular Probes). After several rinses in PBS, the slides were coverslipped with Vectashield (DAPI), and the sections were examined under epifluorescence.

Immunohistochemistry identifying hematopoietic antigen expression on mouse cells.

The spleen and lymph node tissue along with blood and bone marrow smears were rinsed several times in PBS. The tissue was then placed in 1% normal human serum (NhuS) in PBS, 0.5% TritonX100 for 30 minutes at room temperature. The tissue and smears were then stained with the rat monoclonal antibody for CD34 (1:50, Abcam). The next day after several washes in PBS, the slides were incubated with goat anti-rat secondary antibodies conjugated to rhodamine (1:700, Molecular Probes). After several rinses in PBS, the slides were coverslipped with Vectashield (DAPI), and the sections were examined under epifluorescence.

ALDH$^+$ and hUCB cells in primary and secondary lymphoid organs expressing CD34.

Immunohistochemical staining for CD34 cell surface expression of ALDH$^+$ and hUCB cells in the bone marrow resulted in the following findings: (1) transplanted ALDH$^+$ cells were found in bone marrow of G93A mice expressing CD34; and (2) transplanted hUCB cells were found in the bone marrow of G93A mice along with cells expressing CD34.

Immunohistochemical staining for CD34 antigen expression of ALDH$^+$ and hUCB cells in the spleen and lymph nodes of G93A mouse resulted in the following findings: (1) ALDH$^+$ double-labeled cells from the spleen expressed CD34; (2) hUCB double-labeled cells from the spleen were positive for CD34; (3) ALDH$^+$ double-labeled cells from the lymph nodes expressed CD34; (4) hUCB double-labeled cells from the lymph nodes were positive for CD34; and (5) negative expression of hUCB cells for CD34 was indicated in hUCB cells positive for human mitochondria.

Percentage comparisons of differential white blood cell count.

FIG. 1 compares the percentage of lymphocytes and neutrophils present in the peripheral blood from various treated, untreated, and control animals. The normal range of lymphocyte numbers from control animals (C57) averaged between 80-100% whereas, the neutrophil numbers averaged between 10-20%. In untreated G93A SOD1 mice there was a large decrease in the number of lymphocytes and an increase in the number of neutrophils. ALDH-treated mice showed an increase in lymphocyte numbers to 60%, compared to the hUCB and CsA treated groups which averaged between 30-40%. The neutrophil numbers from the CsA and hUCB treated mice were similar (50-60%) and showed an increase compared to the ALDH-treated mice (30-40%).

Immunohistochemical expression of hematopoietic progenitor cell surface marker CD34. Transplanted ALDH+ and hUCB cells were found in the primary and secondary lymphoid organs of G93A mice. These grafted cells expressed the progenitor cell surface marker CD34 in the spleen, lymph nodes, bone marrow, and blood. CD34 positive host cells in were found in the same organs. In the untreated G93A mice, host CD34 positive cells were found in the spleen, lymph nodes, and bone marrow. However, in ALDH$^+$ and hUCB treated groups, CD34 positive cells were not found in the bone marrow. No mouse CD34$^+$ cells were observed in the peripheral blood in any treatment group.

Administered ALDH$^+$ and hUCB cells were found in primary and secondary lymphoid organs of G93A mice after 10-12 weeks cerebral lateral ventricle transplant. Immunohistochemical analysis of hUCB and ALDH$^+$ cells in G93A mice tissues (spleen, lymph node), blood and bone marrow samples, revealed antigen expression for human hematopoietic progenitor cell surface marker CD34. These results indicate natural homing of grafted cells to the primary and secondary lymphoid organs which may indicate engraftment of our administered cells.

There were no host CD34$^+$ cells in peripheral blood in any group of mice. Expression of CD34 was found in host cells in the spleen and lymph node tissues from both treated and untreated mice. Bone marrow cells from untreated G93A mice were positive for CD34 however, host cells from the bone marrow in the ALDH$^+$ and hUCB treated mice did not express CD34. It is unlikely host progenitor cells from the treated mice recapitulated to a more primitive cell. It is reasonable to suggest after treatment host CD34$^+$ cells left the bone marrow to enter other tissues.

At the end-stage of disease in G93A mice, peripheral lymphocyte numbers are greatly reduced and neutrophils are dramatically increased. In the hUCB-treated mice there was a slight increase in neutrophil percentage and a slight decrease in lymphocyte percentage, compared to the untreated G93A mice. Conversely, in the ALDH-treated mice there was a decrease in the percentage of neutrophils and an increase in the percentage of lymphocytes, bringing it closer to low normal levels. ALDH$^+$ cells may increase the immunocompetence of the host by enhancing hematopoietic reconstitution of peripheral white blood cell counts Example 2

To determine whether UCB cells expressed neural markers ells were cultured either in the presence or absence of RA+NGF and then examined using microarray gene technology, RT-PCR, Western blot and immunohistochemistry. With the microarray, there were 322 genes that were both up- or down-regulated by a factor of at least two and the profile of genes and proteins expressed were associated with neurogenesis. RT-PCR revealed that the neural markers musashi, pleiotrophin and nestin were increased in the RA+NGF cultures. Western blots and immunohistochemistry of the cultures confirmed the presence of Musashi-1, β-tubulin-III protein, pleiotrophin, GFAP and NeuN in both treated and untreated cells.

When the UCB cells were transplanted into the anterior subventricular zone (SVZ) of the neonatal rat brain, approximately 30% of transplanted UCB cells survived (without immunosuppression). Further, some cells expressed neuronal (β-tubulin class III or Tuj1) and glial markers (GFAP) after exposure to instructive signals from the developing brain[16].

UCB cells improved behavioral function in a rodent model of stroke, the middle cerebral arterial occlusion (MCAO) model. UCB cells were implanted either intracranially (ic) or intravenously (iv) 24 hours after permanent MCAO. At 1 month post-transplant, UCB transplanted animals showed significantly less spontaneous night activity than lesioned controls. Activity was similar at 1 and 2 months post-transplant and during the light-phase exhibited a similar behavioral pattern. Interestingly, there did not appear to be a significant difference in behavioral recovery between UCB-ic and UCB-iv animals.

In another study, rats were treated iv (tail vein) with UCB cells ($3\times10^6$) either 24 hours or 7 days after MCAO and behavioral performance (rotorod and a neurological exam (mNSS)) was measured. Treatment 24 hours after MCAO significantly improved functional recovery on both tests ($p<0.05$) but with cell transplants 7 days after stroke function improved only on the mNSS ($p<0.05$). UCB cells were observed mainly in the cortex and striatum of the injured hemisphere in the ischemic boundary zone. Few cells were found in the contralateral hemisphere. Some UCB cells were immunoreactive for the neuronal marker NeuN (2%) and MAP-2 (3%); the astrocytic marker GFAP (6%) and the endothelial cell marker FVIII (8%). UCB cells were also detected outside the brain in bone marrow (3%) and spleen (1%); muscle, heart, lung, and liver (0.01% to 0.5%).

UCB cells ($5\times10^5$) were implanted unilaterally into the lateral ventricle of SOD1 (G93A) mouse model of ALS at 7 weeks of age. Ten-eleven weeks after transplantation, immunostaining of UCB cells with antibody against human nuclei showed the survival of implanted cells and the wide distribution of these cells in the ventricular system of the brain (FIG. 1). Some cells were found intraparenchymally. This result indicates that UCB cells can migrate away from the original site of transplantation, and then reach the target area of degenerating neurons.

Together, these data indicate that the UCB cells can differentiate into neural phenotypes that could be used to repair the injured or defective nervous system and therefore produce a viable treatment for ALS.

It will be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described.

What is claimed is:

1. A method of treating a subject with a neurodegenerative disorder, comprising the steps of:
    isolating at least one aldehyde dehydrogenase-expressing progenitor cell from human umbilical cord blood;
    administering to the subject a therapeutically effective amount of the isolated aldehyde dehydrogenase-expressing progenitor cell to a subject suffering from the neurodegenerative disorder; and
    wherein the neurodegenerative disorder is amyotrophic lateral sclerosis, and where the administration improves balance, coordination, physical condition, motor-planning, or a combination thereof in the subject.

2. The method of claim 1 wherein the therapeutically effective amount of the aldehyde dehydrogenase-expressing progenitor cell is administered intravenously.

3. The method of claim 1 further comprising the step of administering an immunosuppressant to the subject following the therapeutically effective amount of the aldehyde dehydrogenase-expressing progenitor cell.

4. The method of claim 1 wherein the therapeutically effective amount of aldehyde dehydrogenase expressing progenitor cells is about 9,000 cells.

5. A method of treating a subject with a neurodegenerative disorder, comprising the steps of:
    isolating at least one aldehyde dehydrogenase expressing progenitor cell from human umbilical cord blood;
    administering to the subject a therapeutically effective amount of the isolated progenitor cell; and
    wherein the neurodegenerative disorder is amyotrophic lateral sclerosis, and where the administration increases lymphocyte percentages and decreases neutrophil percentages in the subject.

6. The method of claim 1 wherein the cells are administered via intrathecal injection.

7. The method of claim 5 wherein the therapeutically effective amount of aldehyde dehydrogenase expressing progenitor cells is about 9,000 cells.

8. The method of claim 5 wherein the therapeutically effective amount of the aldehyde dehydrogenase-expressing progenitor cell is administered intravenously.

9. The method of claim 5 further comprising the step of administering an immunosuppressant to the subject following the therapeutically effective amount of the aldehyde dehydrogenase-expressing progenitor cell.

10. The method of claim 5 wherein the cells are administered via intrathecal injection.

* * * * *